United States Patent [19]

Hirose et al.

[11] Patent Number: 4,567,180

[45] Date of Patent: Jan. 28, 1986

[54] CARBOXIMIDE DERIVATIVE AND MEDICINES CONTAINING SAME

[75] Inventors: Noriyasu Hirose, Tokyo; Shigeru Souda; Kazutoshi Miyake, both of Ibaraki; Shizuo Kuriyama, Saitama; Kazuyasu Usuki; Yasuhiro Akiyama, both of Tokyo; Naoko Nagaoka; Hidetoshi Kawashima, both of Ibaraki, all of Japan

[73] Assignee: Eisai Co., Ltd., Tokyo, Japan

[21] Appl. No.: 555,211

[22] Filed: Nov. 22, 1983

[30] Foreign Application Priority Data

Nov. 25, 1982 [JP] Japan ................................ 57-205545

[51] Int. Cl.[4] ................. A61K 31/505; A61K 31/495; C07D 403/14; C07D 403/06
[52] U.S. Cl. ..................................... 514/253; 544/295; 544/364; 544/372; 544/373
[58] Field of Search ............... 544/295, 373, 364, 372; 424/250, 251; 514/253

[56] References Cited

PUBLICATIONS

Lucas, *Organic Chemistry*, Sec. Ed., 1953, Amer. Book Co., N.Y., pp. 109–110, 212 and 220–221.
Hirose, et al., "Chemical Abstracts", vol. 98, 1982, col. 98:126160u.
"Chemical Abstracts", vol. 101, 1984, col. 101:110951x.

*Primary Examiner*—Glennon H. Hollrah
*Assistant Examiner*—James H. Turnipseed
*Attorney, Agent, or Firm*—Wenderoth, Lind & Ponack

[57] ABSTRACT

A carboximide derivative represented by the general formula:

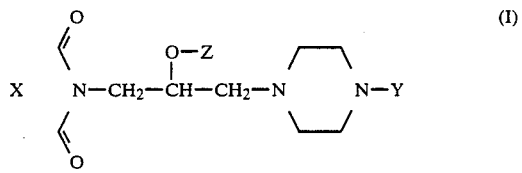

wherein X is

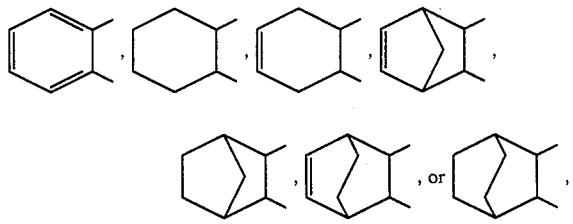

Z is alkyl, aralkyl, cycloalkyl, cycloalkylalkyl, alkenyl or arylalkenyl, and Y is a substituted or unsubstituted pyridyl, pyrimidyl or phenyl group, and a pharmaceutically acceptable acid addition salt thereof. The carboximide derivative and acid addition salt are useful for treating diabetes and also for depressing the central nervous system. The carboximide derivative may be produced by reacting a sodium alkoxide represented by the general formula:

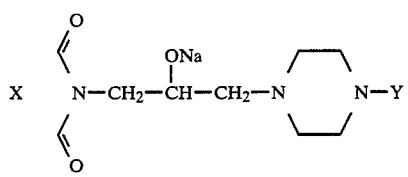

wherein X and Y have the same meanings as defined above, with Z.Hal wherein Hal is a halogen and Z has the same meaning as defined above.

38 Claims, No Drawings

CARBOXIMIDE DERIVATIVE AND MEDICINES CONTAINING SAME

BACKGROUND OF THE INVENTION

This invention relates to novel carboximide derivatives and their pharmaceutically acceptable acid addition salts having excellent medicinal activities, to processes for their production, to medicines containing the same, and to methods for treating diabetes or depressing the central nervous system by the administration thereof.

The carboximide derivatives and their pharmaceutically acceptable acid addition salts are novel compounds. Their chemical structures are considerably different from those of sulfonyl urea agents, biguanide agents and the like which have been widely used to date.

SUMMARY OF THE INVENTION

The present inventors have unexpectedly found that these novel carboximide derivatives and their pharmaceutically acceptable acid addition salts have hypoglycemic activities, and are thus useful as medicines for treating diabetes.

A further investigation has resulted in a surprising finding that the carboximide derivatives and their pharmaceutically acceptable acid addition salts also have activities to depress the central nervous system.

An object of this invention is to provide novel carboximide derivatives and their pharmaceutically acceptable acid addition salts which are useful as medicines for treating diabetes, and also as central nervous system depressants.

Another object of this invention is to provide processes for producing such novel carboximide derivatives and their pharmaceutically acceptable acid addition salts.

A further object of this invention is to provide novel pharmaceutical compositions useful for treating diabetes, or as central nervous system depressants, which compositions contain the novel carboximide derivatives or their pharmaceutically acceptable acid addition salts as active ingredients.

A still further object of this invention is to provide methods for treating diabetes or depressing the central nervous system by the administration of the novel carboximide derivatives or their pharmaceutically acceptable acid addition salts.

In one aspect of this invention, there is thus provided a carboximide derivative represented by the general formula (I):

$$X\diagup\!\!\diagdown N-CH_2-CH(O-Z)-CH_2-N\diagup\!\!\diagdown N-Y \quad (I)$$

wherein X is (structures shown)

Z is alkyl, aralkyl, cycloalkyl, cycloalkylalkyl, alkenyl or arylalkenyl, and Y is a substituted or unsubstituted pyridyl, pyrimidyl or phenyl group, and a pharmaceutically acceptable acid addition salt thereof.

In another aspect of this invention, there is provided a process for producing the carboximide derivative or pharmaceutically acceptable acid addition salt thereof, which comprises reacting a sodium alkoxide represented by the formula (II):

$$X\diagup\!\!\diagdown N-CH_2-CH(ONa)-CH_2-N\diagup\!\!\diagdown N-Y \quad (II)$$

wherein X and Y have the same meanings as defined above, with a halide represented by the formula (III):

$$Z.Hal \quad (III)$$

wherein Hal is a halogen atom and Z has the same meaning as defined above, and, where the pharmaceutically acceptable acid addition salt is desired, further reacting the carboximide derivative with the corresponding acid.

In a further aspect of this invention, there is provided a pharmaceutical composition for treating diabetes, or depressing the central nervous system, which comprises, as an active ingredient, the carboximide derivative or pharmaceutically acceptable acid addition salt thereof.

In a still further aspect of this invention, there is provided a method for treating diabetes, which method comprises administering to a patient suffering from diabetes an effective amount of the carboximide derivative or pharmaceutically acceptable acid addition salt thereof.

In a still further aspect of this invention, there is provided a method for depressing the central nervous system of a patient, which method comprises administering to the patient an effective amount of the carboximide derivative or pharmaceutically acceptable salt thereof.

DETAILED DESCRIPTION OF THE INVENTION

Where X means in formula (I), X may exist in stereoisomeric forms, in other words, as exo, endo, cis and trans forms. All of these stereoisomers are encompassed by the present invention.

For Z, the alkyl groups include, for example, those containing 1–16 carbon atoms, especially straight-chain alkyl containing 1–10 carbon atoms; the aralkyl groups include, for example, those where the aryl group is phenyl and the alkyl group contains 1–4 carbon atoms, and the aryl group may be substituted, for example, by one or two halogen atoms; the cycloalkyl groups include, for example, those containing 3–7 carbon atoms; the cycloalkylalkyl groups include, for example, those where the cycloalkyl group contains 3–7 carbon atoms and the alkyl group contains 1–4 carbon atoms; the alkenyl groups include, for example, those containing 2–10 carbon atoms; and the arylalkenyl groups include, for example, those where the aryl group is phenyl and the alkenyl group contains 2–4 carbon atoms.

For Y, each of the pyridyl, pyrimidyl and phenyl groups may be unsubstituted or substituted. The substituents include, for example, alkyl of 1–4 carbon atoms, halogen and trifluoromethyl. There may be, for example, 1 or 2 such substituents.

As mentioned above, a carboximide derivative of the formula (I) may be readily converted to a pharmaceutically acceptable acid addition salt by reacting the derivative with an inorganic or organic acid. As illustrative acids useful for the production of such salts, there may be mentioned inorganic acids such as hydrochloric acid, hydrobromic acid, sulfuric acid and the like, as well as organic acids such as maleic acid, fumaric acid, succinic acid, acetic acid, malonic acid, citric acid, oxalic acid, benzoic acid and the like.

When producing a carboximide derivative of the formula (I) in accordance with the above-described process of this invention, it is acceptable to use, for example, dioxane, dimethylformamide, dimethylsulfoxide, sulforan or the like as a reaction solvent.

The reaction between compounds (II) and (III) may be carried out under any conditions which are effective to produce the desired compound (I). For example, the reaction may be carried out between 1–2 moles of (III) per mole of (II) at a temperature of from room temperature to the boiling point of the solvent until (I) is formed, more particularly, 50°–100° C. for 2–12 hours The compounds according to this invention have excellent glucose tolerance improving activities and are thus useful as medicines for treating diabetes.

In the case of medicines for treating diabetes, long-term continuous administration is indispensable due to the nature of the illness. The compounds according to this invention have low toxicities. Here again, the present invention is believed to be important.

When a compound according to this invention is used as a medicine for treating diabetes or as a central nervous system depressant, it is administered by the oral or parenteral route (i.e., intramuscularly, subcutaneously or intravenously, or as suppositories, or by another suitable administration technique). Although its dosage may vary depending on the severity of the condition of the patient, it generally ranges from 20 mg to 1,000 mg, preferably from 50 mg to 250 mg, per day for a human adult.

In order to form the compounds according to this invention into suitable dosage forms, they are made into such forms as tablets, granules, powders, capsules, injectable solution, suppositories, etc. in accordance with routine techniques employed in this field.

More specifically, for preparing a solid preparation for oral administration, the active ingredient is mixed with an excipient and, if necessary, further additives such as a binder, disintegrator, lubricant, coloring agent, flavoring agent and the like, and then formed into tablets, coated tablets, granules, powders, capsules, etc. by methods known per se in the art.

Examples of the excipients include milk sugar, corn starch, white sugar, glucose, sorbitol, microcrystalline cellulose, etc.. On the other hand, illustrative binders include polyvinyl alcohol, polyvinyl ether, ethylcellulose, methylcellulose, gum arabic, tragacanth gum, gelatin, shellac, hydroxypropylcellulose, hydroxypropylstarch, polyvinyl pyrrolidone and the like. As illustrative disintegrators, there may be mentioned starch, agar, gelatin powder, microcrystalline cellulose, calcium carbonate, sodium hydrogencarbonate, calcium citrate, dextrin, pectin, etc. Lubricants include magnesium stearate, talc, polyethylene glycol, silica, hardened vegetable oil, etc.. Illustrative coloring agents include those permitted for incorporation in medicines. As flavoring agents, use may be made of, for example, cocoa powder, menthol, aromatic acids, mint oil, camphol, cinnamon powder, etc.. These tablets, granules and the like may of course be suitably coated with sugar, gelatin or the like.

For preparing an injectable solution, the active ingredient is mixed with a pH-adjusting agent, buffer, stabilizer, preservative, etc. and then formed into liquid preparations for subcutaneous, intramuscular or intravenous injection by a method known per se in the art.

Examples of the present invention are set forth below in order to describe this invention in more detail. However, the present invention is by no means limited to these examples.

EXAMPLE 1

N-[2-Ethoxy-3-(4-(2-pyridyl)piperazin-1-yl)propyl]-endo-cis-bicyclo[2.2.1] hept-5-ene-2,3-dicarboximide dimaleate 55% Sodium hydride (0.8 g) was suspended in anhydrous dioxane (50 ml), to which was added dropwise, under nitrogen gas stream and at room temperature, a solution which had been obtained by dissolving N-[2-hydroxy-3-{4-(2-pyridyl)piperazin-1-yl}propyl]-endo-cis-bicyclo[2.2.1]hept-5-ene-2,3-dicarboximide (5.7 g) in dioxane. The resulting mixture was heated to 60° C. and stirred for 1 hour. Thereafter, ethyl iodide (3.0 g) was added dropwise and the thus formed mixture was heated to 75° C. and stirred for 5 hours. After cooling the reaction mixture, ice water was added to the reaction mixture. It was extracted with chloroform. The extract was washed with water and then dried with anhydrous magnesium sulfate. It was thereafter filtered and the filtrate was concentrated. The residue was subjected to silica gel chromatography (developer: a 98:2 mixture of chloroform and ethanol) to obtain N-[2-ethoxy-3-{4-(2-pyridyl)piperazin-1-yl}propyl]-endo-cis-bicyclo[2.2.1]-hept-5-ene-2,3-dicarboximide (yield: 49%). It was recrystallized from a mixed solvent of isopropyl ether and n-hexane. Its melting point was 99°–102° C. A portion (1.64 g) of the thus obtained dicarboximide derivative was then dissolved in ethyl acetate, followed by addition of maleic acid (0.93 g) dissolved in a mixed solvent of ethyl acetate and methanol. The resulting mixture was heated. By allowing the reaction mixture to cool, the desired compound was caused to precipitate. It was collceted by filtration (yield: 2.45 g).

Melting point (°C.): 136–138.

Elemental Analysis for $C_{23}H_{30}N_4O_3.2C_4H_4O_4$:

|  | C | H | N |
|---|---|---|---|
| Calculated (%) | 57.93 | 5.97 | 8.72 |
| Found (%) | 57.85 | 5.95 | 8.74 |

EXAMPLE 2

N-[2-n-Butoxy-3-{4-(2-pyridyl)piperazin-1-yl)propyl]-endo-cis-bicyclo[2.2.1]hept-5-ene-2,3-dicarboximide dimaleate 55% Sodium hydride (1.05 g) was suspended in anhydrous dioxane (60 ml), to which a solution of N-[2-hydroxy-3-{4-(2-pyridyl)piperazin-1-yl}propyl]-endo-cis-bicyclo[2.2.1]hept-5-ene-2,3-dicarboximide (7.64 g) in dioxane was added dropwise under nitrogen gas stream and at room temperature. The resulting mixture was heated to 65° C. and stirring for 1 hour. n-Butyl bromide (3.2 g) was added dropwise at 40° C. and the resulting mixture was agitated for 6 hours at 75°–80° C. After cooling the reaction mixture, ice water was added thereto and it was then extracted with ether. The extract was washed with water and then dried with anhydrous magnesium sulfate. It was filtered and the filtrate was concentrated. Mineral oil contained in the residue, derived from sodium hydride, was washed off with n-hexane. The yield of the thus obtained N-[2-n-butoxy-3-{4-(2-pyridyl)piperazin-1-yl}propyl]-endo-cis-bicyclo[2.2.1]hept-5-ene-2,3-dicarboximide was 3.7 g (yield: 42%). It was then taken up in ethyl acetate, followed by addition of maleic acid (2.0 g) dissolved in a mixed solvent of ethyl acetate and methanol. The resulting mixture was then heated. The resulting reaction mixture was allowed to cool and the desired compound was hence caused to precipitate. The desired compound was collected by filtration, and had the following physical properties (yield: 4.9 g).

Melting point (°C.): 126–129.

Elemental Analysis: for $C_{25}H_{34}N_4O_3.2C_4H_4O_4$:

|  | C | H | N |
|---|---|---|---|
| Calculated (%) | 59.08 | 6.32 | 8.35 |
| Found (%) | 58.81 | 6.32 | 8.44 |

EXAMPLE 3

N-[2-Cyclohexylmethoxy-3-{4-(2-pyridyl)piperazin-1-yl}propyl]-endo-cis-bicyclo[2.2.1]hept-5-ene-2,3-dicarboximide dimaleate 55% Sodium hydride (0.85 g) was suspended in anhydrous dioxane (50 ml), followed by dropwise addition of N-[2-hydroxy-3-{4-(2-pyridyl)piperazin-1-yl}propyl]-endo-cis-bicylo[2.2.1]hept-5-ene-2,3-dicarboximide (5.7 g) dissolved in dioxane (60 ml) under nitrogen gas stream and at room temperature. The resulting mixture was heated to 65°–70° C. and stirred for 1 hour. Cyclohexylmethyl bromide (4.0 g) was added dropwise at 40° C. and the thus formed mixture was stirred at 80°–85° C. for 10 hours. After cooling the reaction mixture, ice water was added to the mixture and the resulting mixture was extracted with ether. The extract was washed with water and then dried with anhydrous magnesium sulfate. It was filtered and the filtrate was concentrated. The residue was subjected to silica gel chromatography (developer: a 98:2 mixture of chloroform and ethanol) to obtain 3.9 g of N-[2-cyclohexylmethoxy-3-{4-(2-pyridyl)-piperazin-1-yl}propyl]-endo-cis-bicyclo [2.2.1]hept-5-ene-2,3-dicarboximide [Rf value: 0.5 (developer: a 96:4 mixture of chloroform and ethanol); yield: 54%]. The reaction product was then dissolved in ethyl acetate, followed by addition of a solution which had been obtained by dissolving maleic acid (1.9 g) in a mixed solvent of ethyl acetate and methanol. The resulting mixture was heated. It was then allowed to cool to cause the desired compound to precipitate. The precipitate was collected by filtration to obtain the desired compound having the following physical properties (yield: 4.5 g).

Melting point (°C.): 137–140.

Elemental Analysis for $C_{28}H_{38}N_4O_3.2C_4H_4O_4$:

|  | C | H | N |
|---|---|---|---|
| Calculated (%) | 60.82 | 6.53 | 7.88 |
| Found (%) | 60.82 | 6.49 | 7.83 |

EXAMPLE 4

N-[2-Allyloxy-3-{4-(2,4-dimethylphenyl)piperazin-1-yl}propyl]-phthalimide oxalate 55% Sodium hydride (0.65 g) was suspended in anhydrous dioxane (30 ml), followed by dropwise addition of N-[2-hydroxy-3-{4-(2,4-dimethylphenyl)piperazin-1-yl}propyl]-phthalimide (4.7 g) dissolved in dioxane (50 ml) under nitrogen gas stream and at room temperature. The resulting mixture was heated to 60° C. and stirred for 1 hour. Then, allyl bromide (1.8 g) was dropped slowly into the mixture at 40° C. and the thus formed mixture was stirred for 3 hours over a water bath at 75° C. The reaction mixture was thereafter cooled, ice water was added thereto, and it was then extracted with ether. After washing the extract twice with water, it was dried with anhydrous magnesium sulfate. The resulting mixture was filtered and the filtrate was concentrated. After washing out the mineral oil, derived from sodium hydride, with n-hexane, the residue was dissolved in ethyl acetate, followed by addition of a solution which had been obtained by dissolving oxalic acid (1.2 g) in ethyl acetate. After heating the resulting mixture, a small amount of IPE (isopropyl ether) was added. The thus obtained mixture was allowed to cool. Precipitated crystals were collected by filtration to obtain the desired compound (4.3 g; yield 69%).

Melting point (°C.): 146–149.

Elemental Analysis for $C_{26}H_{31}N_3O_3.C_2H_2O_4$:

|  | C | H | N |
|---|---|---|---|
| Calculated (%) | 64.22 | 6.37 | 8.03 |
| Found (%) | 64.15 | 6.12 | 7.90 |

EXAMPLE 5

N-[2-Ethoxy-3-{4-(3-chlorophenyl)piperazin-1-yl}-propyl]-endo-cis-bicyclo[2.2.1]heptane-2,3-dicarboximide oxalate N-[2-Ethoxy-3-{4-(3-chlorophenyl)piperazin-1-yl}-propyl]-endo-cis-bicyclo[2.2.1]hept-5-ene-2,3-dicarboximide (1.7 g) was dissolved in a mixed solvent of ethanol (30 ml) and ethyl acetate (10 ml), and then catalytically reduced using 10% palladium-carbon as a catalyst. After confirming by T.L.C. that the raw material had been completely used up, the catalyst was separated by filtration and the filtrate was concentrated. The residue was dissolved in ethyl acetate, followed by addition of a solution containing oxalic acid (500 mg) in ethyl acetate. The resulting mixture was heated to dissolve solid materials completely. A small amount of isopropyl ether was added to the reaction mixture, which was then finally cooled to obtain the desired compound (1.9 g; yield: 74%).

Melting point (°C.) 158–160.
Elemental Analysis for $C_{24}H_{32}N_3O_3Cl.C_2H_2O_4$:

|  | C | H | N |
|---|---|---|---|
| Calculated (%) | 58.25 | 6.41 | 7.84 |
| Found (%) | 58.28 | 6.32 | 7.92 |

Following the procedure of Example 1, the following compound was obtained:

N-[2-Ethoxy-3-{4-(2-pyridyl)piperazin-1-yl}propyl]phthalimide dimaleate

Melting point (°C.): 135–137.
Elemental Analysis for $C_{22}H_{26}N_4O_3.2C_4H_4O_4$:

|  | C | H | N |
|---|---|---|---|
| Calculated (%) | 57.49 | 5.48 | 8.94 |
| Found (%) | 57.25 | 5.40 | 8.96 |

Repeating the procedure of Example 2, the following compounds were obtained.

N-[2-Benzyloxy-3-{4-(2-pyridyl)piperazin-1-yl}propyl]-endo-cis-bicylo[2.2.1]hept-5-ene-2,3-dicarboximide dimaleate Melting point (°C.): 114–117.
Elemental Analysis for $C_{28}H_{32}N_4O_3.2C_4H_4O_4$:

|  | C | H | N |
|---|---|---|---|
| Calculated (%) | 61.35 | 5.73 | 7.95 |
| Found (%) | 61.07 | 5.64 | 7.92 |

N-[2-Allyloxy-3-{4-(2-pyridyl)piperazin-1-yl}propyl]-endo-cis-bicyclo[2.2.2]oct-5-ene-2,3-dicarboximide dimaleate Melting point (°C.) 114–117.
Elemental Analysis for $C_{25}H_{32}N_4O_3.2C_4H_4O_4$:

|  | C | H | N |
|---|---|---|---|
| Calculated (%) | 59.26 | 6.04 | 8.38 |
| Found (%) | 59.02 | 6.02 | 8.20 |

N-[2-(4-Chlorobenzyloxy)-3-{4-(2-pyrimidyl)piperazin-1-yl}-propyl]-endo-cis-bicyclo[2.2.1]hept-5-ene-2,3-dicarboximide maleate Melting point (°C.): 162–164.
Elemental Analysis for $C_{27}H_{30}ClN_5O_3.C_4H_4O_4$:

|  | C | H | N |
|---|---|---|---|
| Calculated (%) | 59.65 | 5.50 | 11.22 |
| Found (%) | 59.74 | 5.27 | 11.14 |

Following the procedure of Example 3, the following compounds were obtained.

N-[2-(n-Octyloxy)-3-{4-(2-pyridyl)piperazin-1-yl}propyl]-cis-cyclohex-4-ene-1,2-dicarboximide 1.7 oxalate Melting point (°C.): 109–112.
Elemental Analysis for $C_{29}H_{43}N_3O_3.1.7C_2H_2O_4$:

|  | C | H | N |
|---|---|---|---|
| Calculated (%) | 61.30 | 7.38 | 6.62 |
| Found (%) | 61.02 | 7.53 | 6.65 |

N-[2-n-Butoxy-3-{4-(3-chlorophenyl)piperazin-1-yl}propyl]-endo-cis-bicylo[2.2.1]hept-5-ene-2,3-dicarboximide oxalate Melting point (°C.): 122–125.
Elemental Analysis for $C_{26}H_{34}ClN_3O_3.C_2H_2O_4$:

|  | C | H | N |
|---|---|---|---|
| Calculated (%) | 59.82 | 6.47 | 7.48 |
| Found (%) | 59.62 | 6.58 | 7.35 |

N-[2-Ethoxy-3-{4-(3-chlorophenyl)piperazin-1-yl}propyl]-endo-cis-bicyclo[2.2.1]hept-5-ene-2,3-dicarboximide oxalate Melting point (°C.): 159–161.
Elemental Analysis for $C_{24}H_{30}ClN_3O_3.C_2H_2O_4$:

|  | C | H | N |
|---|---|---|---|
| Calculated (%) | 58.47 | 6.05 | 7.87 |
| Found (%) | 58.27 | 6.04 | 7.83 |

N-[2-n-Decyloxy-3-{4-(3-chlorophenyl)piperazin-1-yl}propyl]-endo-cis-bicyclo[2.2.1]hept-5-ene-2,3-dicarboximide oxalate Melting point (°C.): 119–122.
Elemental Analysis for $C_{32}H_{46}ClN_3O_3.C_2H_2O_4$:

|  | C | H | N |
|---|---|---|---|
| Calculated (%) | 63.18 | 7.50 | 6.50 |
| Found (%) | 63.03 | 7.37 | 6.51 |

N-[2-n-Butoxy-3-{4-(3-chlorophenyl)piperazin-1-yl}propyl]-cis-cyclohex-4-ene-1,2-dicarboximide 1.1 oxalate Melting point (°C.): 116–119.
Elemental Analysis for $C_{25}H_{34}ClN_3O_31.1C_2H_2O_4$:

| | C | H | N |
|---|---|---|---|
| Calculated (%) | 58.21 | 6.52 | 7.51 |
| Found (%) | 58.09 | 6.69 | 7.36 |

N-[2-n-Butoxy-3-{4-(4-chlorophenyl)piperazin-1-yl}propyl]-endo-cis-bicylo[2.2.1]hept-5-ene-2,3-dicarboximide oxalate Melting point (°C.): 152–155.
Elemental Analysis for $C_{26}H_{34}ClN_3O_3.C_2H_2O_4$:

| | C | H | N |
|---|---|---|---|
| Calculated (%) | 59.82 | 6.47 | 7.48 |
| Found (%) | 59.60 | 6.61 | 7.46 |

N-[2-n-Butoxy-3-{4-(2-chlorophenyl)piperazin-1-yl}-propyl]-endo-cis-bicylo[2.2.1]hept-5-ene-2,3-dicarboximide dioxalate Melting point (°C.): 109–112.
Elemental Analysis for $C_{26}H_{34}ClN_3O_3.2C_2H_2O_4$:

| | C | H | N |
|---|---|---|---|
| Calculated (%) | 55.27 | 5.89 | 6.45 |
| Found (%) | 55.49 | 6.10 | 6.67 |

The procedure of Example 4 was repeated to obtain the following compounds.

N-[2-Allyloxy-3-{4-(2-pyridyl)piperazin-1-yl}propyl]phthalimide 1.2 oxalate

Melting point (°C.): 130–133.
Elemental Analysis for $C_{25}H_{29}N_3O_4.1.2C_2H_2O_4$:

| | C | H | N |
|---|---|---|---|
| Calculated (%) | 60.09 | 5.80 | 7.73 |
| Found (%) | 60.09 | 5.80 | 7.63 |

N-[2-Benzyloxy-3-{4-(3-chlorophenyl)piperazin-1-yl}propyl]-endo-cis-bicylo[2.2.1]hept-5-ene-2,3-dicarboximide oxalate Melting point (°C.): 168–170.
Elemental Analysis for $C_{29}H_{32}ClN_3O_3.C_2H_2O_4$:

| | C | H | N |
|---|---|---|---|
| Calculated (%) | 62.45 | 5.76 | 7.05 |
| Found (%) | 62.71 | 5.81 | 6.96 |

N-[2-Cinnamyloxy-3-{4-(α,α,α-trifluoro-3-tolyl)piperazin-1-yl}-propyl]-endo-cis-bicyclo[2.2.1]hept-5-ene-2,3-dicarboximide oxalate Melting point (°C.): 164–166.
Elemental Analysis for $C_{32}H_{34}F_3N_3O_3.C_2H_2O_4$:

| | C | H | N |
|---|---|---|---|
| Calculated (%) | 62.27 | 5.54 | 6.41 |
| Found (%) | 62.38 | 5.57 | 6.41 |

Following the procedure of Example 5, the following compounds were obtained.

N-[2-n-Octyloxy-3-{4-(2-pyridyl)piperazin-1-yl}propyl]-cyclohexane-1,2-dicarboximide 1.7 oxalate Melting point (°C.): 120–123.
Elemental Analysis for $C_{29}H_{45}N_3O_3.1.7C_2H_2O_4$:

| | C | H | N |
|---|---|---|---|
| Calculated (%) | 61.10 | 7.68 | 6.60 |
| Found (%) | 61.00 | 7.65 | 6.63 |

N-[2-n-Butoxy-3-{4-(3-chlorophenyl)piperazin-1-yl}propyl]-endo-cis-bicyclo[2.2.1]heptane-2,3-dicarboximide oxalate Melting point (°C.): 123–125.
Elemental Analysis for $C_{26}H_{36}ClN_3O_3.C_2H_2O_4$:

| | C | H | N |
|---|---|---|---|
| Calculated (%) | 59.61 | 6.80 | 7.45 |
| Found (%) | 59.49 | 6.77 | 7.48 |

N-[2-n-Decyloxy-3-{4-(3-chlorophenyl)piperazin-1-yl}propyl]-endo-cis-bicyclo[2.2.1]heptane-2,3-dicarboximide oxalate Melting point (°C.): 120–123.
Elemental Analysis for $C_{32}H_{48}ClN_3O_3.C_2H_2O_4$:

| | C | H | N |
|---|---|---|---|
| Calculated (%) | 62.98 | 7.79 | 6.48 |
| Found (%) | 62.93 | 7.66 | 6.57 |

N-[2-n-Butoxy-3-{4-(4-chlorophenyl)piperazin-1-yl}propyl]-endo-cis-bicyclo[2.2.1]heptane-2,3-dicarboximide oxalate Melting point (°C.): 152–155.
Elemental Analysis for $C_{26}H_{36}ClN_3O_3.C_2H_2O_4$:

| | C | H | N |
|---|---|---|---|
| Calculated (%) | 59.61 | 6.80 | 7.45 |
| Found (%) | 59.22 | 7.03 | 7.34 |

N-[2-n-Butoxy-3-{4-(2-chlorophenyl)piperazin-1-yl}propyl]-endo-cis-bicyclo[2.2.1]heptane-2,3-dicarboximide 1.7 oxalate Melting point (°C.): 108–111.
Elemental Analysis for $C_{26}H_{36}ClN_3O_3.1.7C_2H_2O_4$:

| | C | H | N |
|---|---|---|---|
| Calculated (%) | 56.29 | 6.35 | 6.70 |
| Found (%) | 56.03 | 6.40 | 6.79 |

Next, exemplary preparations containing representative compounds of this invention will be described.

Preparation Example 1: Tablets

| | |
|---|---|
| N—[2-Ethoxy-3-{4-(2-pyridyl)piperazin- | 50 g |

| -continued | |
|---|---|
| 1-yl}propyl]phthalimide dimaleate | |
| Corn starch | 10 g |
| Milk sugar | 65 g |
| Calcium carboxymethylcellulose | 10 g |
| Polyvinyl pyrrolidone | 5 g |
| Talc | 10 g |
| Microcrystalline cellulose | 50 g |

In accordance with methods known per se in the art, all the above ingredients were mixed, granulated and then press-formed into tablets, each of 200 mg.

Preparation Example 2: Capsules

| N—[2-n-Butoxy-3-{4-(3-chlorophenyl)-piperazin-1-yl}propyl]-cis-cyclohex-4-ene-1,2-dicarboximide 1.1 oxalate | 50 g |
|---|---|
| Milk sugar | 45 g |
| Corn starch | 5 g |

The above composition was prepared into capsules, each containing 100 mg, in a manner known per se in the art.

Having now fully described the invention, it will be apparent to one of ordinary skill in the art that many changes and modifications can be made thereto without departing from the spirit or scope of the invention as set forth herein.

What is claimed is:

1. A compound selected from the group consisting of a carboximide of the formula

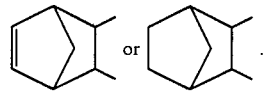

wherein
X is

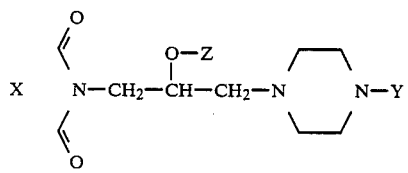

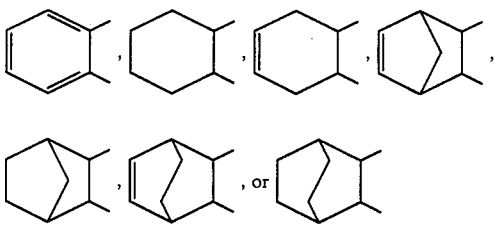

Z is (1) alkyl of 1–10 carbon atoms, (2) benzyl in which the phenyl moiety is unsubstituted or is substituted by a halogen atom, (3) cyclohexyl, (4) cyclohexylmethyl, (5) allyl or (6) cinnamyl, and Y is pyridyl, pyrimidyl or phenyl, said groups being unsubstituted or substituted by at least one member selected from the group consisting of halogen and methyl, and a pharmaceutically acceptable acid addition salt thereof.

2. A compound according to claim 1, wherein X is

3. A compound according to claim 1, wherein Y is 2-pyridyl.

4. A compound according to claim 1, wherein Y is 2-chlorophenyl, 3-chlorophenyl or 4-chlorophenyl.

5. A compound according to claim 1, wherein Y is 2,4-dimethylphenyl.

6. A compound according to claim 1, wherein Y is α,α,α-trifluoro-3-tolyl.

7. A compound according to claim 1, wherein Z is a straight-chain alkyl group containing 1–10 carbon atoms.

8. A compound according to claim 7, wherein the straight-chain alkyl group is ethyl, n-butyl, n-octyl or n-decyl.

9. A compound according to claim 1, wherein Z is substituted or unsubstituted benzyl.

10. A compound according to claim 1, wherein Z is allyl.

11. A compound according to claim 1, wherein Z is cinnamyl.

12. A pharmaceutically acceptable acid addition salt according to claim 1, wherein the salt is a hydrochloride, hydrobromide, sulfate, maleate, fumarate, succinate, acetate, malonate, citrate, oxalate or benzoate.

13. A compound according to claim 1, which is N-[2-ethoxy-3-{4-(2-pyridyl)piperazin-1-yl}propyl]-endo-cis-bicyclo[2.2.1]-hept-5-ene-2,3-dicarboximide or the dimaleate thereof.

14. A compound according to claim 1, which is N-[2-n-butoxy-3-{4-(2-pyridyl)piperazin-1-yl}propyl]-endo-cis-bicyclo[2.2.1]-hept-5-ene-2,3-dicarboximide or the dimaleate thereof.

15. A compound according to claim 1, which is N-[2-cyclohexylmethoxy-3-{4-(2-pyridyl)piperazine-1-yl}propyl]-endo-cis-bicyclo-[2.2.1]hept-5-ene-2,3-dicarboximide or the dimaleate thereof.

16. A compound according to claim 1, which is N-[2-allyloxy-3-{4-(2,4-dimethylphenyl)piperazin-1-yl}propyl]-phthalimide or the oxalate thereof.

17. A compound according to claim 1, which is N-[2-ethoxy-3-{4-(3-chlorophenyl)piperazin-1-yl}propyl]-endo-cis-bicyclo[2.2.1]heptane-2,3-dicarboximide or the oxalate thereof.

18. A compound according to claim 1, which is N-[2-ethoxy-3-{4-(2-pyridyl)piperazin-1-yl}propyl]-phthalimide or the dimaleate thereof.

19. A compound according to claim 1, which is N-[2-benzyloxy-3-{4-(2-pyridyl)piperazin-1-yl}propyl]-endo-cis-bicyclo[2.2.1]hept-5-ene-2,3-dicarboximide or the dimaleate thereof.

20. A compound according to claim 1, which is N-[2-allyloxy-3-{4-(2-pyridyl)piperazin-1-yl}propyl]-endo-cis-bicyclo[2.2.2]oct-5-ene-2,3-dicarboximide or the dimaleate thereof.

21. A compound according to claim 1, which is N-[2-(4-chlorobenzyloxy)-3-{4-(2-pyrimidyl)piperazin-1-yl}propyl]-endo-cis-bicyclo[2.2.1]hept-5-ene-2,3-dicarboximide or the maleate thereof.

22. A compound according to claim 1, which is N-[2-(n-octyloxy)-3-{4-(2-pyridyl)piperazin-1-yl}propyl]-ciscyclohex-4-ene-1,2-dicarboximide or the 1.7 oxalate thereof.

23. A compound according to claim 1, which is N-[2-n-butoxy-3-{4-(3-chlorophenyl)piperazin-1-yl}propyl]-endo-cis-bicyclo[2.2.1]hept-5-ene-2,3-dicarboximide or the oxalate thereof.

24. A compound according to claim 1, which is N-[2-ethoxy-3-{4-(3-chlorophenyl)piperazin-1-yl}propyl]-endo-cis-bicyclo[2.2.1]hept-5-ene-2,3-dicarboximide or the oxalate thereof.

25. A compound according to claim 1, which is N-[2-n-decycloxy-3-{4-(3-chlorophenyl)piperazin-1-yl}propyl]-endo-cis-bicyclo[2.2.1]hept-5-ene-2,3-dicarboximide or the oxalate thereof.

26. A compound according to claim 1, which is N-[2-n-butoxy-3-{4-(3-chlorophenyl)piperazin-1-yl}propyl]-cis-cyclohex-4-ene-1,2-dicarboximide or the 1.1 oxalate thereof.

27. A compound according to claim 1, which is N-[2-n-butoxy-3-{4-(4-chlorophenyl)piperazin-1-yl}propyl]-endo-cis-bicyclo[2.2.1]hept-5-ene-2,3-dicarboximide or the oxalate thereof.

28. A compound according to claim 1, which is N-[2-n-butoxy-3-{4-(2-chlorophenyl)piperazin-1-yl}propyl]-endo-cis-bicyclo[2.2.1]hept-5-ene-2,3-dicarboximide or the dioxalate thereof.

29. A compound according to claim 1, which is N-[2-allyloxy-3-{4-(2-pyridyl)piperazin-1-yl}propyl]phthalimide or the 1.2 oxalate thereof.

30. A compound according to claim 1, which is N-[2-benzyloxy-3-{4-(3-chlorophenyl)piperazin-1-yl}propyl]-endo-cis-bicyclo[2.2.1]hept-5-ene-2,3-dicarboximide or the oxalate thereof.

31. A compound according to claim 1, which is N-[2-cinnamyloxy-3-{4-(α,α,α-trifluoro-3-tolyl)piperazin-1-yl}propyl]-endo-cis-bicyclo[2.2.1]hept-5-ene-2,3-dicarboximide or the oxalate thereof.

32. A compound according to claim 1, which is N-[2-n-octyloxy-3-{4-(2-pyridyl)piperazin-1-yl}propyl]-cyclohexane-1,2-dicarboximide or the 1.7 oxalate thereof.

33. A compound according to claim 1, which is N-[2-n-butoxy-3-{4-(3-chlorophenyl)piperazin-1-yl}propyl]-endo-cis-bicyclo[2.2.1]heptane-2,3-dicarboximide or the oxalate thereof.

34. A compound according to claim 1, which is N-[2-n-decyloxy-3-{4-(3-chlorophenyl)piperazin-1-yl}propyl]-endo-cis-bicyclo[2.2.1]heptane-2,3-dicarboximide or the oxalate thereof.

35. A compound according to claim 1, which is N-[2-n-butoxy-3-{4-(4-chlorophenyl)piperazin-1-yl}propyl]-endo-cis-bicyclo[2.2.1]heptane-2,3-dicarboximide or the oxalate thereof.

36. A compound according to claim 1, which is N-[2-n-butoxy-3-{4-(2-chlorophenyl)piperazin-1-yl}propyl]-endo-cis-bicyclo[2.2.1]heptane-2,3-dicarboximide or the 1.7 oxalate thereof.

37. A pharmaceutical composition for treating diabetes, or depressing the central nervous system, which comprises, as an active ingredient, and effective amount of a carboximide of the formula

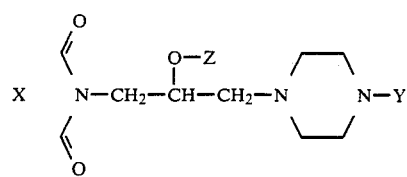

wherein
X is

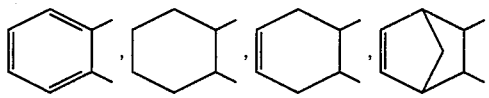

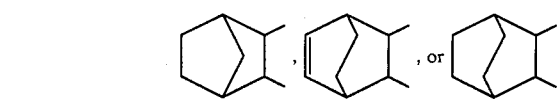

Z is (1) alkyl of 1–10 carbon atoms, (2) benzyl in which the phenyl moiety is unsubstituted or is substituted by a halogen atom, (3) cyclohexyl, (4) cyclohexylmethyl, (5) allyl or (6) cinnamyl, and Y is pyridyl, pyrimidyl or phenyl, said groups being unsubstituted or substituted by at least one member selected from the group consisting of halogen and methyl, or a pharmaceutically acceptable acid addition salt thereof, and a pharmaceutically acceptable carrier therefor.

38. A method for treating diabetes which comprises administering to a patient suffering from diabetes a therapeutically effective amount of a carboximide of the formula:

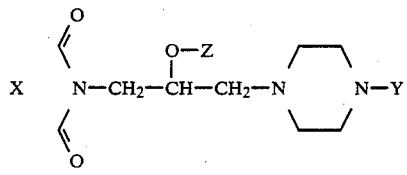

wherein
X is

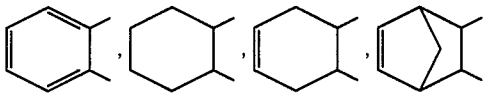

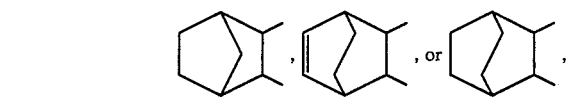

Z is (1) alkyl of 1–10 carbon atoms, (2) benzyl in which the phenyl moiety is unsubstituted or is substituted by a halogen atom, (3) cyclohexyl, (4) cyclohexylmethyl, (5) allyl or (6) cinnamyl, and Y is pyridyl, pyrimidyl or phenyl, said groups being unsubstituted or substituted by at least one member selected from the group consisting of halogen and methyl, or a pharmaceutically acceptable acid addition salt thereof.

* * * * *